US00PP08411P

United States Patent [19]

Saville

[11] Patent Number: Plant 8,411

[45] Date of Patent: Oct. 12, 1993

[54] MINIATURE ROSE PLANT NAMED SAVAKLIM

[75] Inventor: F. Harmon Saville, Rowley, Mass.

[73] Assignee: Nor'East Miniature Roses, Inc., Rowley, Mass.

[21] Appl. No.: 983,463

[22] Filed: Nov. 30, 1992

[51] Int. Cl.[5] ..... A01H 5/00

[52] U.S. Cl. ..... Plt./3

[58] Field of Search ..... Plt. 8.2, 3, 7.1

*Primary Examiner*—Howard J. Locker
*Assistant Examiner*—E. F. McElwain
*Attorney, Agent, or Firm*—Christie, Parker & Hale

[57] ABSTRACT

A new climbing miniature rose with yellow flowers of good form.

1 Drawing Sheet

SUMMARY OF THE INVENTION

The present invention relates to a new and distinct variety of climbing rose plant of the miniature rose class, which was created by me by crossing as seed parent the variety known as 'Ferris Wheel' and as pollen parent the variety known as 'Golden Jubilee'. The varietal denomination of this new rose is 'Savaklim'.

Among the novel characteristics possessed by this new variety which distinguishes it from its parent and all other varieties of which I am aware is its attractive yellow flowers of good form.

Asexual reproduction by propagation of cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is resonably possible to make the same in a color illustration of this character. Phenotypic expression may vary with light availability and cultural conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:
*Seed parent.*—'Ferris Wheel'.
*Pollen parent.*—'Golden Jubilee'.
Class: Miniature.

The following observations are made of specimens grown under glass in Essex Country, Mass., during the month of October.

FLOWER

Blooming habit: Recurrent.

A. Bud:
(1) *Size.*—Medium.
(2) *Form.*—Pointed.

(3) *Color.*—As sepals divide, bud color is near 6A.
(4) *Sepals.*—Longer than bud, slight foliation.
(5) *Peduncle.*—Length — about ¾ inch. Aspect — Straight. Strength — Erect. Color — Near 143B.

B. Bloom:
(1) *Size.*—Average size when fully expanded — About 1⅝ inches in diameter.
(2) *Borne.*—Singly and several together in small sprays.
(3) *Form.*—Cupped, petals loose.
(4) *Petalage.*—Number of petals under normal conditions — About 15.
(5) *Color.*—After sepals divide, petal top and undersurface appear as near 6A. Reverse of petals is near 12A. Color near point of petal attachment is also near 6A. General tonality from a distance is bright yellow. As flowers age, coloring becomes lighter, approaching near 158B after three or more days.

C. Petals:
(1) *Texture.*—Average.
(2) *Appearance.*—Inside velvety and outside satiny.
(3) *Form.*—Fan shaped, without apex.
(4) *Arrangement.*—Imbricated-regularly arranged, shingle-like.
(5) *Petaloids in center.*—Few.
(6) *Persistence.*—Drop off cleanly.
(7) *Fragrance.*—Slight.
(8) *Lasting quality.*—Average.

REPRODUCTIVE ORGANS

A. Stamens, filaments and anthers:
*Arrangement and color.*—Regularly arranged around styles. Color — Near 17B.

B. Pollen:
*Color.*—Near 17A.

C. Styles: Medium length, thin.

D. Stigmas:
*Color.*—Near 4D.

E. Hips:
*Shape.*—Globular.
*Size.*—About ½ inch.
*Color.*—Near 28B.
*Seeds.*—Occasionally protrude.

PLANT

A. Form: Climbing growth habit, upright.

B. Growth: Very vigorous.
*Height attained.*—About 4 to 5 feet.

C. Foliage: Compound 5 to 7 leaflets.

(1) *Size.*—Medium.

(2) *Quantity.*—Abundant.

(3) *Color.*—New foliage: Upper side — Near 143A. Underside — Near 146C. Old foliage: Upper side — Near 139A. Underside — Near 146B.

(4) *Shape.*—Oval, pointed.

(5) *Texture.*—Upper side is semi-glossy; underside is matte.

(6) *Edge.*—Serrated.

(7) *Serration.*—Regular, fine.

(8) *Leaf stem.*—Color — Near 137C. Underside — 146B.

(9) *Stipules.*—Medium length, smooth.

(10) *Resistance to disease.*—Blackspot — Better than average. Mildew — Better than average. Rust — Better than average.

D. Wood:

(1) *New wood.*—Color — Near 143A. Bark — Smooth.

(2) *Old wood.*—Color — Near 143A. Bark — Smooth.

E. Thorns:

*Quantity (main stalk).* — Very few.

*On laterals from stalk.*—Few.

*Form.*—Small, downward pointing, very thin.

*Length.*—About ¼ inch.

*Color.*—Near 184B.

*Position.*—Irregular.

*Prickles.*—None.

F. Winter hardiness: Needs protection in severe climates.

I claim:

1. A new and distinct variety of climbing rose plant of the miniature rose class, substantially as shown and described.

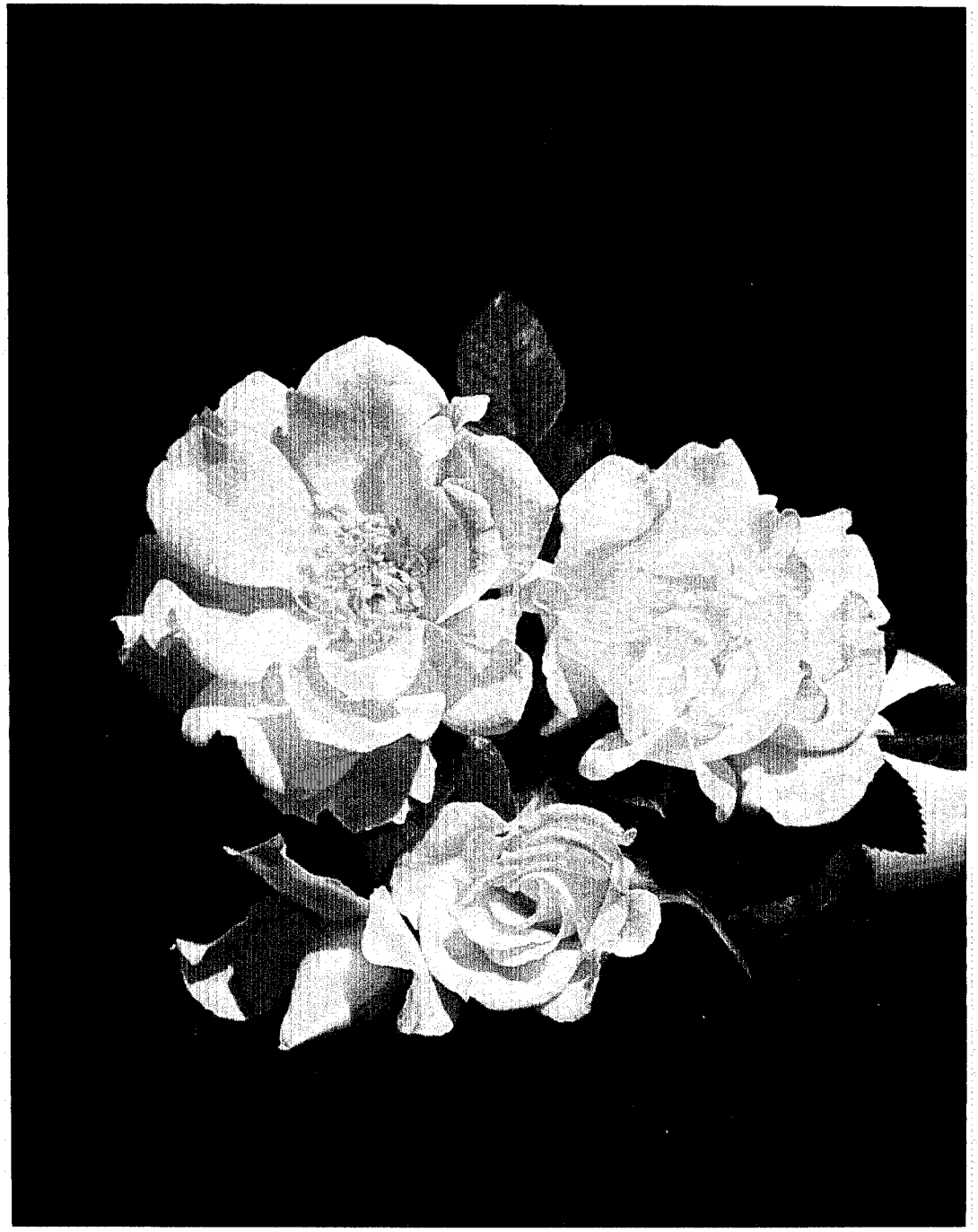

* * * * *